(12) United States Patent
Erbacher et al.

(10) Patent No.: US 9,102,935 B2
(45) Date of Patent: Aug. 11, 2015

(54) NUCLEIC ACID PURIFICATION METHOD

(75) Inventors: Christoph Erbacher, Haan (DE); Roland Fabis, Leverkusen (DE)

(73) Assignee: Qiagen GmbH, Hilden (DE)

( * ) Notice: Subject to any disclaimer, the term of this patent is extended or adjusted under 35 U.S.C. 154(b) by 1052 days.

(21) Appl. No.: 13/141,878

(22) PCT Filed: Dec. 23, 2009

(86) PCT No.: PCT/EP2009/067909
§ 371 (c)(1),
(2), (4) Date: Sep. 12, 2011

(87) PCT Pub. No.: WO2010/072834
PCT Pub. Date: Jul. 1, 2010

(65) Prior Publication Data
US 2011/0319506 A1  Dec. 29, 2011

(30) Foreign Application Priority Data
Dec. 23, 2008 (DE) .......................... 10 2008 063 001

(51) Int. Cl.
*G01N 30/96* (2006.01)
*C12N 15/10* (2006.01)

(52) U.S. Cl.
CPC .................................. *C12N 15/1006* (2013.01)

(58) Field of Classification Search
None
See application file for complete search history.

(56) References Cited

U.S. PATENT DOCUMENTS

| 5,324,591 | A | * | 6/1994 | Georger et al. | ............... 428/552 |
| 6,103,479 | A | * | 8/2000 | Taylor | ............... 506/14 |
| 2001/0014650 | A1 | * | 8/2001 | Smith et al. | ............... 502/401 |
| 2001/0018513 | A1 | * | 8/2001 | Baker | ............... 536/25.41 |
| 2007/0197780 | A1 | | 8/2007 | Park et al. | |

FOREIGN PATENT DOCUMENTS

| WO | WO00/69872 | 11/2000 |
| WO | WO2008/035991 | 3/2008 |
| WO | WO2008/097342 | 8/2008 |

* cited by examiner

*Primary Examiner* — Robert T Crow
(74) *Attorney, Agent, or Firm* — Fanelli Haag PLLC

(57) ABSTRACT

The present invention relates to a method for purifying nucleic acids using a nucleic acid-binding phase which is furnished with a deficit of nucleic acid-binding groups A having a pK of 8 to 13, or which has groups A and binding-inhibiting groups N which are neutrally charged during the binding, and preferably during the elution, and the method comprises the following steps: (a) binding the nucleic acids to the nucleic acid-binding phase at a pH which is below the pH of the pK of the nucleic acid-binding groups A (binding pH); (b) eluting the nucleic acids at a pH which is above the binding pH (elution pH). In addition, corresponding kits and also nucleic acid-binding phases which can be used for purifying nucleic acids are disclosed. The technology according to the invention permits the purification of nucleic acids and, in particular, elution, with use of low salt concentrations, and so the purified nucleic acids can be directly processed, for example used in a PCR.

21 Claims, 7 Drawing Sheets

Support material according to Claim 2(i)

A)

B)

Support material

Compound bearing a group A

Compound bearing a group N

Starter molecule T

Support material according to Claim 2(iii)

For legend see Figure 1

= sterically shielding oligomers or polymers bearing the group N

Compound bearing a sterically shielding group N

Support material according to Claim 2(iv)

For legend see Figure 1

Compound bearing a sterically shielding group N

A) Support material according to Claim 3

B) Conventional support material

Support material

Compound bearing a group A

NUCLEIC ACID PURIFICATION METHOD

This application is a National Stage of PCT/EP2009/067909, filed Dec. 23, 2009 which claims priority to German Application No. 10 2008 063001.2, filed Dec. 23, 2008, the disclosures of which are incorporated herein by reference in their entirety.

The present invention relates to a method of and a kit for purifying nucleic acids using a nucleic acid-binding support material. In addition, suitable methods of purifying appropriate support materials are described.

Various methods of purifying and isolating nucleic acids have been disclosed in the prior art, including the use of phenol chloroform, salting-out methods, the use of ion exchangers and silica particles.

A known method of purifying nucleic acids is the "charge-switch method". This involves contacting a nucleic acid-binding phase containing primarily weakly basic polymers such as poly Bis-Tris, poly Tris, polyhistidine, polyhydroxylated amines, chitosan or triethanolamine at a first pH with a nucleic acid-containing sample, during which the nucleic acid-binding phase has a positive charge. This promotes binding of the negatively charged nucleic acids to said phase. To release/elute the nucleic acids, a second pH which is higher than the pKa of the nucleic acid-binding phase is set according to the charge-switch principle, in order to invert or neutralize the positive charge. Setting the pH to above the pKa of the nucleic acid-binding groups of the solid phase promotes detachment of the bound nucleic acids from the nucleic acid-binding phase.

The prior art has disclosed both soluble phases (see, for example, EP 0 707 077) and solid phases (see, for example, WO 99/29703). Various solutions are used for elution, for example solutions having a very high pH or else biological buffers, in particular low-salt buffers such as, for example Tris buffers.

The purified nucleic acids are usually processed further. Said further processes comprise, for example, amplifications such as polymerase chain reaction (PCR), enzymic reactions such as restriction, ligation, phosphorylation, dephosphorylation or RNA transcription, hybrid capture assays and electrophoresis. These "downstream" reactions often have little tolerance of relatively high salt concentrations, and therefore a desalting step must frequently be carried out prior to processing the nucleic acids.

An elution buffer that does not contain too much salt and furthermore is not too basic is therefore desirable for the immediate subsequent usage of the purified nucleic acids, without additional buffer-changing or desalting steps.

The elution performance of anion exchanges, however, increases as a function of an increase in the pH and the salt concentration of the elution buffer. The chromatographic requirements therefore directly contradict the requirements regarding DNA processing. Consequently, the prior art tries to promote specifically the elution of nucleic acids by selecting suitable nucleic acid-binding groups and pH conditions.

Notwithstanding the known methods of purifying nucleic acids, there is a need for improving the existing methods, more specifically for purifying the nucleic acids in such a way that the sample can also be processed immediately thereafter.

It is therefore an object of the present invention to provide a method of purifying nucleic acids, which enables the sample to be processed immediately thereafter. More specifically, the invention is Intended to make available a method that allows elution at low salt concentrations.

This object is achieved according to the present invention by a method of purifying nucleic acids, which employs a special nucleic acid-binding phase.

According to a first embodiment, the nucleic acid-binding phase has nucleic acid-binding groups A having a pKa of from 8 to 13, and also groups N which weaken binding and which have a neutral charge at the binding pH used.

The method of purification using this nucleic acid-binding phase has the following steps:
(a) binding of the nucleic acids to the nucleic acid-binding phase at a pH which is below the pK of the nucleic acid-binding groups A (binding pH);
(b) elution of the nucleic acids at a pH which is above the binding pH (elution pH).

The present invention relates to the purification of nucleic acids by means of a nucleic acid-binding phase which also has binding-weakening groups N in addition to nucleic acid-binding groups A. According to the invention, the nucleic acid-binding groups A have a pKa of from 8 to 13. The nucleic acids are bound at a pH below the pKa of at least one of said groups A. The groups A therefore take up a proton and, as a result, become positively charged, enabling the nucleic acid-binding phase to bind the negatively charged nucleic acids. The elution is carried out at a pH above the binding pH, thereby reducing the positive charge of the nucleic acid-binding phase.

The additional groups N are charge-neutral at the binding pH and preferably also at the elution pH. The groups N therefore influence in several aspects the binding strength of the groups A: (1.) They interrupt the arrangement of the groups A and, due to the reduced density of A groups, therefore influence the strength of binding of the nucleic acids to the nucleic acid-binding phase. (2.) They can by way of functional groups which can enter into weak interactions (e.g. via van der Waals interactions) to interactions of medium strength (e.g. via hydrogen bonds) specifically modulate the strength of binding. (3.) The groups N can, with increasing size and/or number, sterically shield the nucleic acid-binding groups A and thereby reduce the strength of binding. The groups N therefore cause a uniform, pH-independent reduction in the strength of nucleic acid binding. As a result of this, fewer nucleic acids are bound which can then be detached more readily from the nucleic acid-binding phase. The function of the groups N is that of reducing in a specific and controlled manner the binding strength and/or number of the groups A and thereby setting a desired frequency in the nucleic acid-binding phase according to the invention. The higher the proportion of groups N, the lower the proportion of groups A and the lower the charge density and the weaker the binding of nucleic acids to the nucleic acid-binding phase. The ratio of groups A to groups N can be specifically adjusted by means of the preparation process in order to enable the desired strength of nucleic acid binding to be established beforehand in the or by the method of preparing the corresponding nucleic acid-binding phase (for example by polymerization, (poly)condensation and in particular by coating of a support material).

A considerable advantage of this is that of being able to carry out the elution under conditions which allow the eluted nucleic acids to be processed further immediately after purification. A multiplicity of biotechnological methods such as, for example, amplification of nucleic acids (in particular by means of PCR), sequencing, reverse transcription, restriction analyses, and others (see above) are sensitive to contaminations in the eluate, in particular to high salt concentrations. The purification method according to the invention allows advantageously the elution at low salt concentrations or low ionic strength, thereby enabling immediate further processing in a subsequent biotechnological method, in particular a PCR reaction.

The concept of weakening the attachment of the nucleic acids by employing the groups N leads to surprisingly good results. The prior art assumes optimal binding of the nucleic acid for method optimization and then concentrates on optimizing the conditions of binding and in particular elution. In contrast, a weakening of the binding strength was considered to be disadvantageous with respect to the yield to be expected, for example because the nucleic acids bind in the binding step only insufficiently to the nucleic acid-binding phase or could be eluted during washing. In the view of this, the concept according to the invention of successful and gentle purification of nucleic acids despite a reduction in binding strength due to the presence of groups N must be considered as an extreme surprise.

The proportion of A groups, based on the N groups, can be from 1% to 99%, 1 to 50%, preferably 1% to 25%.

According to a preferred embodiment, the nucleic acid-binding phase is modified in order to introduce the groups A and N. According to the invention, this involves various embodiments which will be illustrated in more detail below.

According to one embodiment, the nucleic acid-binding phase is provided with different ligands (ligands I and ligands II), with the ligands I having at least one group A and the ligands II having at least one group N. This embodiment is illustrated in FIG. 1A. The groups A and N are then in direct proximity, and polymer coatings can also be formed. Due to the presence of N-group-carrying ligands II, the number of groups A decreases, thereby reducing the tightness of binding of the nucleic acids, in particular when a support material is used. Owing to the groups N, the density of groups A on the support surface is therefore reduced, and consequently the binding affinity for the nucleic acids is reduced. As a result, the nucleic acids can be eluted more readily. The term "ligand" or "ligands" refers in particular to a functionalization of the surface, by which preferably a support material is modified with at least one group A and/or one group N, in order to provide the nucleic acid-binding phase according to the invention. The ligands I and II are preferably bound to the support material and may, for example, be monomers, dimers, oligomers or polymers of reactive individual molecules. In one variant, the groups A or the groups N as part of compounds reacting with the support material are bound directly or via a linker or spacer to a support material. According to a preferred embodiment, this modification is achieved by contacting the support material with a mixture having the different ligands I and II. The higher the proportion of ligand II with respect to ligand I, the lower the strength of binding to the nucleic acid. This ratio can be controlled simply by a corresponding ratio of the ligand I and ligand II reactants in the coating process. Details are illustrated below and in connection with the synthesis or the method of preparing a corresponding support material. The ligands may also form a polymer coating. The support material may also be provided with groups A and starter molecules T, with one or more groups N being bound to said starter molecules. This embodiment is depicted in FIG. 1B. The groups N are in this case located "above" the groups A with respect to the surface of the support material. It is also possible to attach the groups A also via starter molecules.

According to a further embodiment of the present invention, the support material is modified with nucleic acid-binding ligands, with one or more groups A and one or more groups N being present within a single ligand. This embodiment is illustrated in more detail in FIG. 2. There are various possibilities of implementing this concept.

According to one variant, the support material is provided with groups A (bound either directly or, for example, via a starter molecule T) which carry one or more compounds containing a group N (see also FIG. 2A). If a plurality of groups N are present, they may also be in the form of an unbranched chain or as a branched tree structure or as a corresponding mixture. This may involve, for example, from 1 to 100 groups N, 1-20, preferably 1-10 and particularly preferably 1-5 groups N per ligand. If desired, still further groups A and N may also be introduced. This linking strategy results in a relatively homogeneous binding plane with a virtually pure A-group occupation and one or more planes which adjoin outwards and reduce the binding strength of groups A due to the occupation with N groups.

According to a further variant of this embodiment, the support material is provided with groups A (bound either directly or, for example, via a starter molecule T), which carry a mixture of N groups and A groups (see also FIG. 2B). This may involve binding first one or more groups A to the support material. This is followed by attaching to these A-containing trunk ligands compounds which introduce at least one or more groups N. Controlling the reaction conditions enables in each case only one group A and N to be present within the ligand; however, the ligands may also be in the form of oligomers or polymers. The ligands designed as oligomers and polymers may have a random distribution of groups N (see, for example, FIG. 2B, right-hand figure), an alternating sequence thereof (see, for example, FIG. 2B, left-hand figure) or else an arrangement thereof as block copolymer. Combinations are also possible. Suitable methods of designing the appropriate A- and N-containing functionalizations/ligands are described in detail below.

According to a further embodiment, the support material is modified with groups A and N, with the groups A being sterically shielded by compounds having at least one, preferably multiple groups N. There are also various variants of this embodiment.

According to one variant, steric shielding is preferably done by oligomers or polymers having groups N. Said oligomers or polymers can be bound, for example, to the ligands having the group(s) A (see also FIG. 3B). However, they may also be arranged adjacent thereto, as long as steric shielding is ensured (see also FIG. 3A). The oligomers/polymers having N groups shield the groups A by way of a kind of cap from the environment by forming more or less ordered secondary structures (e.g. "random coils" or helices), and are therefore capable of weakening binding of the nucleic acids. The oligomers/polymers may also be prepared from the groups N and may also be introduced by way of block copolymers.

This variant may be prepared by applying, for example, in a first step starter groups T to the support material, for example by silanization. In a second step, monomers containing groups A may then be grafted on, for example by means of ATRP (atom transfer radical polymerization). After this monomer has fully reacted, a second monomer having neutral groups N may be introduced. This produces a copolymer on the support, which consists of a first homopolymer carrying anion exchanger groups, and a second homopolymer which is linked to the first one and carries neutral groups N. The length of the nascent polymer chain, and therefore the strength of steric shielding, can be controlled via the amount of the second monomer carrying the groups N.

The extent of steric shielding can therefore be controlled by means of chain length and monomer substitutions. Preferred chain lengths for the oligomers/polymers having N groups are n=10-1000, n=10 to 500, particularly preferably n=10-100. The oligomers/polymers carrying groups N may be designed using the monomers described in the present application, which will be described in detail. Polyacrylates are particularly suitable.

Preferred polymers used are polyacrylates according to the following formula:

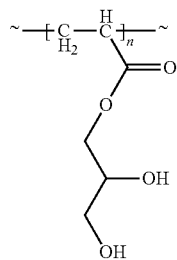

A reagent which is particularly suitable for achieving steric shielding is glycidyl methacrylate, from which neutral diol groups N are produced after hydrolysis. To this end, a starter molecule T may be applied, for example by silanization. This is followed by polymerizing a first monomer, for example an N,N-dimethylaminopropyl methacrylate, on the support, for example by means of ATRP. In a second polymerization step, these groups are then sterically shielded. This may be achieved, for example after the monomers have fully reacted, by introducing a second monomer, for example glycidyl methacrylate, from which neutral diol groups N are produced after hydrolysis. The steric effect prevents close contact of the nucleic acid with the A groups and, as a result, the latter are not bound so strongly and can be eluted at low ionic strength and thus low salt concentration from the nucleic acid-binding phase.

Steric shielding of the groups N may also be achieved by "bulky" substituents, examples of which that may be mentioned are branched alkyl radicals such as iospropyl, diisopropyl, tertiary butyl, aliphatic or aromatic rings, either as carbon rings or as heterocycles. These sterically inhibiting groups N may also be employed in the form of oligomers/polymers.

Steric shielding may therefore be controlled in particular via (i) the proportion of the additionally introduced groups N; (ii) the synthesis of the compounds carrying the group N; (iii) the selection and structure of group N and (iv) the chain length of the oligomers/polymers having N groups.

The group(s) A may therefore be particularly well shielded by groups N which are present in the same ligand or are arranged in proximity thereto. Binding to the group A is also possible. Steric shielding increases as a function of an increase in the size of the compound having the group(s) N and also in the size of group N, with both an increase in the chain length and greater branching of the carbon chains or an increase in the ring size of cyclic groups increasing steric shielding.

In a particular embodiment, the support material is modified using a combination of all linking strategies described above. Examples are shown in FIG. 4. Thus, the support material may have directly linked to one another the groups A, the sterically shielding groups N and starter molecules T, said starter molecules being provided with further sterically shielding groups N (see FIG. 4A, for example). This type of linkage may be carried out using, for example, the customary groups N (see FIG. 4B, for example). The support material may furthermore be provided, for example, with groups A (bound directly or via a starter molecule T) and carry a mixture linked thereto of N groups and A groups, with all or some of the groups N being a sterically inhibiting group (see FIGS. 4D and 4E).

According to a further aspect of the present application, the method is carried out using a nucleic acid-binding phase which has a support material and which is modified with groups A, with only part of the support material being occupied with groups A, meaning that substantially fewer nucleic acid-binding groups are provided than usual. Since therefore fewer nucleic acid-binding groups A are present per unit area of the support material and/or per gram of support material, the binding strength of the nucleic acids is reduced similarly to the previous linking strategies. FIG. 5 depicts an embodiment of this concept. This embodiment therefore also enables the nucleic acids to be eluted under conditions which allow said nucleic acids to be processed further immediately, in particular because low salt concentrations can be employed for eluting the nucleic acid from the nucleic acid-binding phase.

The substoichiometric amount according to the invention of A groups on the support material may be obtained by employing a substoichiometric amount of the compound introducing the group A, in relation to the support material. It is also conceivable that the support material has a smaller amount of potential binding sites to which the groups A can be attached. A further embodiment includes chemical or physical pretreatment of the support material, which causes a reduction in binding sites or a reduced reactivity of said binding sites. A possible alternative strategy is to apply the compound carrying group A in a mixture with another compound which likewise binds to the support material. The competing attachment decreases the proportion of A groups on the surface of the support material.

The embodiment based on a substoichiometric amount of A groups may further be combined with one or more of the above-described embodiments for modifying the support material with groups A and N.

Providing the support with a substoichiometric amount of groups A is particularly advantageous when a silica support material is employed, since the latter has silanol groups. The groups A are introduced preferably by means of silanes or a silane mixture. A minimum amount of silane is required for a complete covering of the support. This minimum amount is defined by the specific surface of the support material. If the amount of silane(s) is insufficient for occupying the surface of the support, the charge density may be reduced. The amount of groups A and thereby the binding strength of the nucleic acid-binding phase can therefore be adjusted via the amount of silane to be applied.

According to one embodiment, the support material has a silica surface which is coated by a silane having groups A, the amount of silane being from 0.1 to 50 μmol (micromol, also referred to here as umol), preferably 0.1 to 10 umol. It is crucial to reduce the amount of silane by so much that the elution is possible at relatively low ionic strength or relatively low (desired) salt concentrations. This can be tested, for example experimentally, and checked by means of a chromatogram. The amount of silane can therefore be optimized preferably depending on the support material employed, in order to achieve the desired binding/elution properties.

The nucleic acid-binding phase is preferably a solid phase. It may be prepared by binding the groups A, the binding-attenuating groups N and the starter molecules T, if present, to a solid support material, for example. Details will be described below. Employing a solid phase facilitates the removal of the bound nucleic acids from the sample. According to one embodiment, binding of the nucleic acids is therefore followed by removing the solid phase or the unbound supernatent.

Examples of supports suitable for the nucleic acid-binding groups are oxidic materials. These are in particular oxides such as $Al_2O_3$, $TiO_2$, $ZrO_2$, $Ta_2O_3$, $SiO_2$ and polysilicic acid, with the preferred support material being $SiO_2$ or polysilicic acids. Suitable supports are also organic polymers such as polystyrene and its derivatives, polyacrylates and polymethacrylates, and their derivatives, or polyurethanes, nylon, polyethylene, polypropylene, polybutylidene and copolymers of these materials. In addition, these nucleic acid-binding groups may also be linked to polysaccharides, in particular hydrogels such as agarose, cellulose, dextran, SEPHADEX® SEPHACRYL® and chitosan. Furthermore, the nucleic acid-binding groups may also be attached to inorganic supports such as, for example, glass or metal surfaces such as gold, for example. Using magnetic particles is particularly advantageous. The nucleic acid-binding groups A and/or the groups N may be bound to these supports directly or else via other chemical molecules, for example starter molecules or linkers. They may also be part of a larger molecule. If the support material does not have any suitable functional groups as binding sites, these may be introduced in a manner known per se.

Further embodiments of the support materials comprise non-magnetic and magnetic particles, column materials, membranes, and surface coatings. Mention should also be made of functionalized supports such as tubes, membranes, nonwovens, paper, reaction vessels such as PCR vessels, "Eppendorf tubes", multiplates, chips and microarrays.

According to one embodiment, the nucleic acid-binding phase is positively charged both during binding and during elution.

A further embodiment of the present invention relates to a soluble nucleic acid-binding phase which reversibly binds the nucleic acids according to the principle according to the invention. Soluble polymers may have groups A and N, for example alternately or randomly (see, for example, FIG. 2B). It is also possible for the side chains of the A groups to be shielded by groups N, in particular alkyl radicals, with examples that may be mentioned being diisopropyl radicals on the nitrogen. The comments in connection with the support material apply accordingly to the soluble nucleic acid-binding phase.

According to one embodiment, the nucleic acid-binding groups A are ion exchangers, preferably anion exchangers. Preferred groups A that are proven in the binding of nucleic acids are amino groups, with primary, secondary and tertiary amino groups being preferred. These may be substituted or unsubstituted. In addition, cyclic amines, aromatic amines or amino-functionalized heterocycles may also be employed. The amines may bear substituents, for example alkyl, alkenyl, alkynyl or aromatic substituents, and in addition, the hydrocarbon chains may also be closed to give a ring. The hydrocarbon chains may also have heteroatoms such as oxygen, nitrogen, sulphur or silicon, or branchings. As stated, the amino groups by way of groups A have a pKa of from 8 to 13, preferably 9 to 13, particularly preferably from 10 to 12.

The group A may be part of a compound which, by means of polymerization or condensation, forms an oligomer or polymer and which is therefore particularly suitable for forming the ligands. Examples of such chain-forming compounds are acrylates containing amino groups, such as N-(3-aminomethyl)methacrylamide, N-(3-aminoethyl)methacrylamide,
N-(3-aminopropyl)methacrylamide, N-(3-aminoisopropyl)methacrylamide,
N,N-dimethylacrylamide, N,N-diethylacrylamide, N,N-diisopropylacrylamide,
N,N-(dimethylamino)ethylacrylamide, N,N-(dimethylamino)ethyl acrylate,
N,N-(dimethylamino)ethylmethacrylamide, N,N-(dimethylamino)ethyl methacrylate,
N,N-(dimethylamino)propylacrylamide, N,N-(dimethylamino)propyl acrylate,
N,N-(dimethylamino)propylmethacrylamide, N,N-(dimethylamino)propyl methacrylate,
N,N-(diethylamino)ethylacrylamide, N,N-(diethylamlno)ethyl acrylate,
N,N-(diethylamino)ethylmethacrylamide, N,N-(diethylamino)ethyl methacrylate,
N,N-(diethylamino)propylacrylamide, N,N-(diethylamino)propyl acrylate,
N,N-(diethylamino)propylmethacrylamide, N,N-(diethylamino)propyl methacrylate,
N,N-(diisopropylamino)ethylacrylamide, N,N-(diisopropylamino)ethyl acrylate,
N,N-(diisopropylamino)ethylmethacrylamide, N,N-(diisopropylamino)ethyl methacrylate,
N,N-(diisopropylamino)propylacrylamide, N,N-(diisopropylamino)propyl acrylate,
N,N-(dimethylamino)propylmethacrylamide, N,N-(dimethylamino)propyl methacrylate, 2-(dimethylamino)ethyl methacrylate (DMAEMA) and 2-(diisopropylamino)ethyl methacrylate.

Of these, N,N-(dimethylamino)propyl methacrylate is particularly preferred.

The group A may be present in a silane, preferably in a reactive silane. Reactive silanes refer to compounds which have hydrolytically unstable Si bonds, for example Si—N or Si—O bonds. Examples of reactive silanes containing at least one group A are:

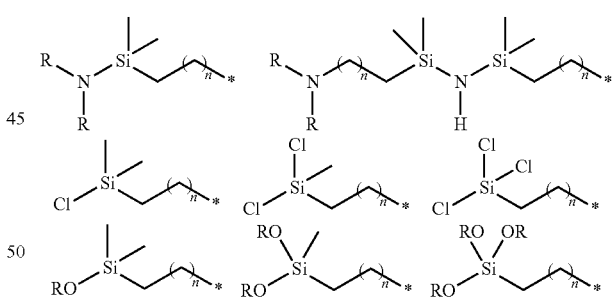

wherein
n is 1 to 5
R is a C1 to C6, preferably a C1 to C3, alkyl group; and
* is amino, aminomethyl, aminoethyl, aminopropyl, dimethylamino, diethylamino, diisopropylamino, dipropylamino, diethanolamino, dipropanolamino, diethylenetriamine, triethylenetetramine, tetraethylenepentamine, etheramine, polyetheramine, 4-diisobutylamino-1-butane, 6-dipropylamino-1-hexane.

Corresponding reactive silanes may be employed for introducing the groups A. Particular preference is given to diethylaminopropyl trimethoxysilane (DEAPS), dim ethylaminopropyl trimethoxysilane and N,N-diisopropylaminopropyl trimethoxysilane.

According to one embodiment of the present invention, the nucleic acids are bound at a pH of from 2 to 8, preferably 4 to 7.5. This refers to the pH during binding and thus in the sample. Depending on the design of the nucleic acid-binding phase, the method according to the invention can therefore also be carried out under very gentle conditions and virtually in the neutral range. Owing to the fact that the protonatable groups of the nucleic acid-binding phase have a pKa of from 8 to 13, preferably 9 to 13 and particularly preferably 10 to 12, they have a sufficient positive charge even at relatively neutral pH, in order to allow effective attachment of the nucleic acids. As a result, binding can be carried out under very gentle conditions, if desired.

Depending on the starting material, at least one customary lysis step may precede the binding step, in order to release the nucleic acids.

Elution of the nucleic acids is another important step of the present method. As stated, the nucleic acids are released at a pH which is above the binding pH. As a result of this, the groups A have a smaller positive charge during elution, which favours release of the nucleic acids. Compared to conventional anion exchangers, the reduced proportion of the groups A and/or the presence of the binding-attenuating groups N lead to reduced binding of the nucleic acids to the support material. As a consequence of this, as stated above, it is possible to carry out the elution also at low salt concentrations.

The elution pH is preferably below the pK of the groups A. Depending on the nucleic acid-binding group A or nucleic acid-binding phase used, the elution is preferably carried out at a pH of from 8 to 11, 8 to 10, preferably at a pH of from 8.0 to 9, particularly preferably 8.5 to 9. It is, however, also possible in principle to use higher pH values. However, the preferred low pH values yield particularly advantageous results because the nucleic acids can be released nevertheless at low salt concentrations and, moreover, the conditions are gentle.

In order to enable the isolated nucleic acids subsequently to be processed immediately in the elution buffer, the latter, as stated, has preferably a low salt concentration. This is made possible by the design according to the invention of the nucleic acid-binding phase. According to one embodiment, the salt concentration is therefore from 1 mM to 1000 mM, particularly preferably from 1 mM to 200 mM, 1 mM to 250 mM, or 1 mM to 100 mM. Suitable salts may be chlorides of the alkali metals and alkaline earth metals or ammonium, other salts of mineral acids, acetates, borates, and compounds such as Tris, Bis-Tris and organic buffers such as, for example, MIS, CHAPS, HEPES, and the like. The same applies to the binding buffer. Suitable substances for elution are moreover known in the prior art. The salt concentration is unchanged in the binding step and in the elution step or is raised slightly during elution. Preferably, however, the concentration is not increased in such a way that subsequent reactions are impaired. Furthermore, the temperature during binding and elution may be the same or is raised during elution.

In order to facilitate purification, preferably at least one washing step is carried out after binding and prior to elution of the nucleic acids. Preference is given to washing with aqueous solutions having low salt concentrations but also with water. Salts present in the washing buffers preferably are at a concentration of 1 mM to 1000 mM, particularly preferably from 1 mM to 200 mM, 1 mM to 250 mM, or 1 mM to 100 mM. The buffer may comprise organic compounds such as carbohydrates and preferably organic solvents such as, for example, alcohols, polyols, polyethylene glycols, ethers, polyethers, dimethyl sulphoxide, acetone or acetonitrile. However, the washing buffers should not have any interfering amounts of the corresponding organic components in order to not impair the downstream applications.

Binding-attenuating groups N which may be used are charge-neutral groups such as hydroxyl groups, diol groups, triol groups, saccharides, epoxide groups, C1-C6 alkyl, alkene or alkyne groups, polyol groups, ethers, polyethers, halides or imides. The use of hydrophilic groups N ensures the continued good wettability of the ion exchangers with aqueous buffers. The group N may be part of a compound which forms an oligomer or polymer due to polymerization or condensation. Examples of compounds capable of introducing the groups N are acrylates such as butyl acrylate, propyl acrylate, ethyl acrylate, methyl acrylate, glycidyl methacrylate, hydroxyethyl methacrylate (HEMA), glycidoxypropyl methacrylate, glycerol mono-methacrylate (isomeric mixture), glycol mono-methacrylate and N-acryloxysuccinimide.

The group N may also be present in a silane, preferably in a reactive silane. Examples of reactive silanes containing the group N are:

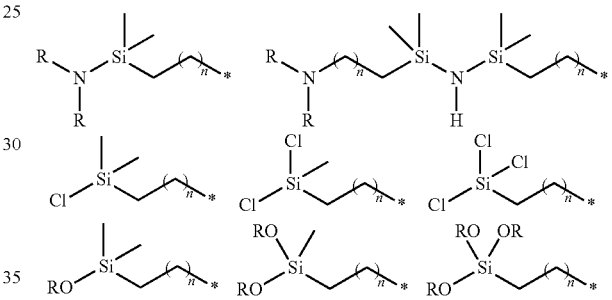

wherein
n is 1-5
R is a C1 to C6, preferably C1 to C3, alkyl group;
* is Hydroxymethyl, hydroxyethyl, hydroxypropyl, ethanediol, propanediol, propanetriol, butanetriol, 3-glycidoxypropyl, ethyl glycidyl ether, alkyl radical, in particular a C1 to C4 alkyl radical, halide or hydrogen.

According to one embodiment, the support material has starter groups T which have been at least partially functionalized with compounds having groups A and/or groups N. Suitable examples will be illustrated in detail hereinbelow.

The invention further relates to the synthesis of or to a method of preparing a corresponding nucleic acid-binding support material. To this end, there are various embodiments:

Alternative (A): This method comprises functionalizing the support material using a mixture of at least two different ligands I and II, with the ligands I having at least one group A and the ligands II having or being at least one group N. Details regarding this embodiment have already been illustrated in detail above. Reference is made to the above disclosure.

Alternative (B): This method comprises functionalizing in a first step the support material using a mixture of starter molecules T and ligands having at least one group A. Here, the compounds bearing a group A have been selected or are modified in such a way that no further molecules can be attached. In a second step, compounds which bear at least one group N and bind to the starter molecules T are then added.

Alternative (C): Functionalization of the support material with nucleic acid-binding ligands, with each of said ligands having one or more groups A and one or more groups N within them. Details are illustrated above in connection with the method according to the invention. Preference is given to attaching in a first step starter molecules T to the support material, which are used as starting point for growing a copolymer chain by adding compounds having at least one group A and/or at least one group N and attaching said compounds to the starter molecules T. The polymer chain is extended by adding further compounds having at least one group A and/or at least one group N.

In this connection, the polymerization steps may also be controlled in such a way that both the groups A and N are incorporated by way of oligomers, thus producing block copolymers. An example of a controlled polymerization reaction which may be employed according to the invention is the "atom transfer radical polymerization" (ATRP), for example. The ATRP is characterized by the concentration of free radicals being reduced by adding a transition metal complex and in combination with an atom transfer process involving an organohalide, to such an extent that chain termination reactions such as disproportionation or recombination are repressed to a very large extent.

Alternative (D): Functionalization of the support material with groups A and N, with the groups A being sterically shielded by compounds having at least one group N. According to one embodiment of this variant, the support material is functionalized in a first step with starter groups T. This is followed by adding compounds having at least one group A and attaching them to the starter molecules T. In a further step, the groups A are shielded by attaching at least one compound having at least one group N. Preference is given to the groups N being oligomers/polymers (see above) which sterically shield the groups A owing to their three-dimensional structure. Details are illustrated above in connection with the method according to the invention.

Alternative (E): According to this embodiment, the support material is functionalized with a substoichiometric amount of groups A. This variant has been described in detail above. Reference is made to the above disclosure.

The alternatives A-E may also be employed in any combination. Details regarding the nucleic acid-binding groups A, the groups N and the starter molecules T have been described in detail above and also apply in connection with the methods of support modification listed here and characterize the components used therein. Reference is made to the above disclosure.

According to one embodiment of the method of functionalizing the support material with the groups A and N, said groups are introduced via monofunctional, bi- or tri-functional reactive silanes or by means of a mixture of at least two reactive silanes with different functions. Reactive silanes which may be used are, for example, aminosilanes, disilazanes, chlorosilanes or alkoxysilanes. The proportion of the A groups with respect to the N groups is from 1% to 99%, 1 to 50%, preferably 1% to 25%.

Tri- and bifunctional reactive silanes tend to form on the support thick layers crosslinked by polycondensation. In contrast, monofunctional reactive silanes react, for example, with the silanol groups of the support material with formation of siloxane (Si—O—Si) bonds, resulting in rather mono-molecular layers on the support. The support material may be reacted with reactive silanes in the gaseous phase or in suspension in a solvent, it being possible to use in the latter organic and preferably aqueous solvents, depending on the chemistry of the reactive silane.

Suitable and preferred support materials have been described in detail above. According to one embodiment of the method, the support material is first modified with starter molecules T, followed by introducing in the next step the groups A and/or groups N in the form of monomers. The starter molecules T may be used by way of an attachment site for further compounds which are introduced, for example, by means of (poly)condensation or polymerization, in particular a free-radical polymerization, such as, in particular, ATRP (atom transfer radical polymerization). Examples of starter molecules T are:

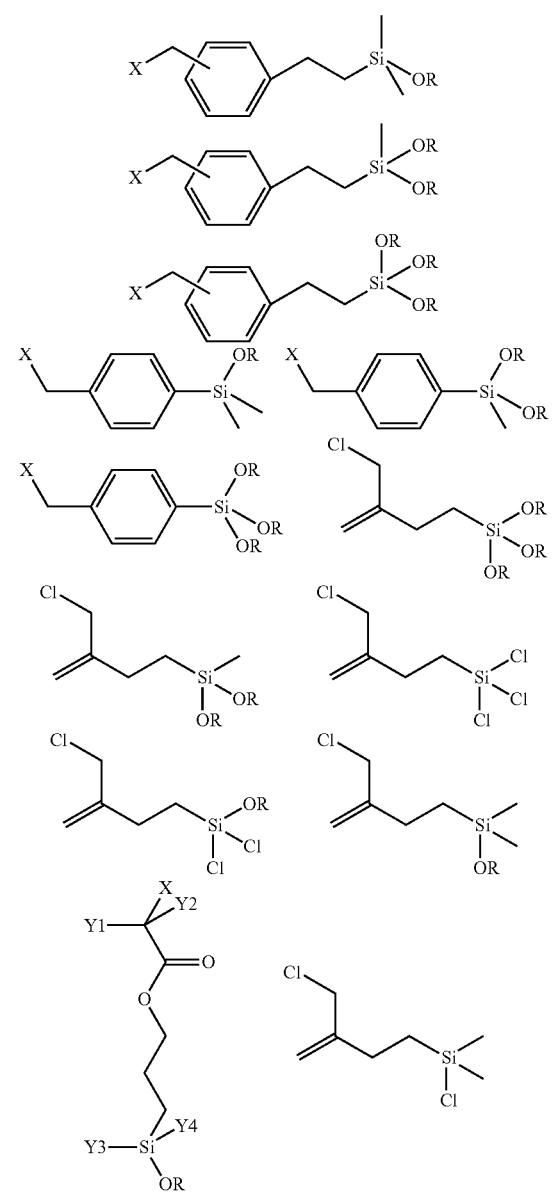

wherein X is halogen, in particular Cl, Br, I

Y1, Y2, Y3 or Y4 are, independently of one another, R, OR, OH or H and R is C1-C3 alkyl.

Preference is given to employing 2-(chloromethyl)allyl trimethoxysilane or [3-(2-bromoisobutyryl)propyl]ethoxydimethylsilane (BPDS) as starter molecule.

Examples of reactive silanes capable of introducing according to the method according to the invention groups A and/or groups N are listed below:

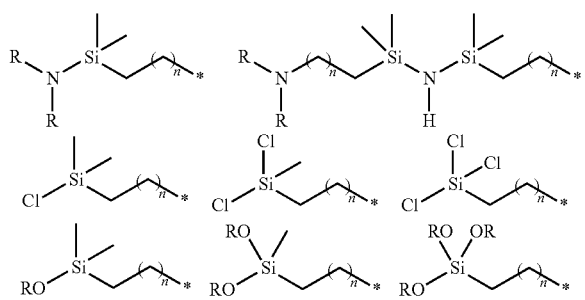

wherein
n is 1-5
R is a C1 to C6, preferably C1 to C3, alkyl group, in particular methyl, ethyl, propyl, isopropyl;
* is amino, aminomethyl, aminoethyl, aminopropyl, dimethylamino, diethylamino, diisopropylamino, dipropylamino, diethanolamino, dipropanolamino, diethylenetriamine, triethylenetetramine, tetraethylenepentamine, etheramine, polyetheramine, 4-diisobutylamino-1-butane, 6-dipropylamino-1-hexane, hydroxymethyl, hydroxyethyl, hydroxypropyl, ethanediol, propanediol, propanetriol, butanetriol, 3-glycidoxypropyl, ethyl glycidyl ether, alkyl radical, in particular a C1 to C4 alkyl radical, in particular methyl, ethyl, propyl, isopropyl, butyl, Isobutyl, halide or hydrogen.

In addition to the methods of mixed silanization and sub-stoichiometric silanization, which have been described in detail, there are other possibilities of adjusting the density of groups A on the support material in a defined manner. As stated, it is possible, for example, to carry out a "grafting-from" process on the support material. This can be achieved, for example, by the method of atom transfer radical polymerization (ATRP) which has been described above. This method comprises firstly applying starter groups T, groups N and/or groups A to the support by means of silanization. The starter groups T are crucial to this process because these groups initiate the grafting-from process (chain initiation).

For example, homopolymers, copolymers and block copolymers can be grown by means of ATRP (Atom Transfer Radical Polymerization) using halide-containing silanes. ATRP is a special form of living/controlled free radical polymerization (LFRP), which comprises concentration of free radicals being reduced by adding a transition metal complex and in combination with an atom transfer process involving an organohalide, to such an extent that chain termination reactions such as disproportionation or recombination are repressed to a very large extent. This method enables the charge density of the support surface to be specifically adjusted by using monomers and monomer mixtures and thereby the binding strength of the nucleic acids to be influenced. The groups A and/or N may be specifically applied by an appropriate choice of monomers.

The nucleic acid-binding support materials generated accordingly may be used in particular in the purification method according to the invention.

The invention further relates to the use of a nucleic acid-binding phase according to the invention for purifying nucleic acids. In accordance with the invention, nucleic acids comprise in particular DNA and RNA, in particular genomic DNA, plasmid DNA, and PCR fragments, cDNA, miRNA, siRNA, and also oligonucleotides and modified nucleic acids such as, for example, PMA or LMA. It is also possible to purify viral or bacterial RNA and DNA or nucleic acids from human, animal or plant sources. Suitable for a purification according to the invention are furthermore also DNA/RNA hybrids and modified nucleic acids.

The invention also provides a kit for purifying nucleic acids, which is characterized in that it has a nucleic acid-binding support material according to the invention, which has nucleic acid-binding groups A that have at least one protonatable group and a pKa of from 8 to 13, preferably 9 to 13, particularly preferably 10 to 12. Details regarding the support material according to the invention and its functionalization are stated above; reference is made to the above comments.

The kit may also have binding, washing and/or elution buffers as described, for example, above in connection with the purification methods. In addition, it may have lysis and neutralization buffers.

According to one embodiment, the kit has a binding buffer which preferably has at least one of the following features:
 (a) a pH of from 1 to 13; and/or
 (b) a salt concentration of from 1 mM to 1000 mM, particularly preferably from 1 mM to 200 mM, 1 mM to 250 mM, or 1 mM to 100 mM.

The advantages of the corresponding features have been illustrated above in connection with the method, and reference is being made to the above disclosure.

According to one embodiment, the kit also has a washing buffer which preferably has at least one of the following features:
 (a) a pH of from 2 to 7, preferably 4 to 7; and/or
 (b) a salt concentration of from 1 mM to 1000 mM, particularly preferably from 1 mM to 800 mM, 1 mM to 600 mM; and/or
 (c) it is selected from the group consisting of water, biological buffers, organic buffers, in particular Tris, Tris-Bis, MIS, MOPS, CHAPS and HEPES.

According to a further embodiment, the kit also has an elution buffer which preferably has at least one of the following features:
 (a) a pH of from 8 to 10, preferably 8 to 9 and/or
 (b) a salt concentration of from 1 mM to 1000 mM, particularly preferably of 1 mM to 200 mM, 1 mM to 250 mM, or 1 mM to 100 mM; and/or
 (c) it is selected from the group consisting of water, biological buffers, organic buffers, in particular Tris, Tris-Bis, MIS, MOPS, CHAPS and HEPES.

Details regarding the nucleic acid-binding phase and the elution conditions are described above and also apply in connection with the kit according to the invention and characterize the components/buffers used therein. Reference is made to the above disclosure.

Kits according to the invention may be applied in particular within the framework of the method according to the invention. The present methods, kits and nucleic acid-binding solid phases may be employed in particular in the field of molecular biology, molecular diagnostics, forensics, food analysis, and applied testing. Applying the kits according to the invention allows the purified nucleic acids to be further processed immediately in "downstream" applications, in particular in a PCR reaction.

By choosing/combining the parameters described, in particular the elution-promoting binding-attenuating groups N, and reduction of the nucleic acid-binding groups, the pH of the nucleic acid-binding phase can be optimized with respect to the elution conditions. Correspondingly, the elution profile of the nucleic acid-binding phase, in particular the salt concentration and the elution pH, can be controlled or adjusted.

Nucleic acids which may be purified by the systems according to the invention may be present in bodily fluids such as blood, urine, stool, saliva, in biological sources such as tissue, cells, in particular animal cells, human cells, plant cells, bacteria cells, and the like, organs such as liver, kidneys or lungs, and it is also possible to obtain the nucleic acid from support materials such as swabs, PapSmears, and stabilizing media such as PRESERVCYT® or SUREPATH®, or else from other liquids such as, for example, juices, aqueous samples or food in general. In addition, the nucleic acids may be obtained from plant material, bacterial lysates, paraffin-embedded tissue, aqueous solutions or gels.

The eluted nucleic acids may preferably be further processed immediately, and thus be employed in a PCR, RT-PCR, a restriction digestion or a transcription, for example. Further purification is not required, as long as the elution buffers are designed as described above and preferably have a low salt concentration.

FIGURES

In the figures:

FIG. 1 depicts a schematic overview of the support material being provided with the nucleic acid-binding groups A and the binding-weakening groups N, with said groups being on separate ligands (see also Claim 2(i)).

FIG. 2 depicts a schematic overview of the support material being provided with the nucleic acid-binding groups A and the binding-inhibiting groups N, said groups being present by way of a mixture within a single ligand (see also Claim 2(ii)). (A) depicts a support material which has been provided firstly with groups A and then with groups N; (B) depicts an alternating sequence of A and N within a single ligand.

Figure 1:
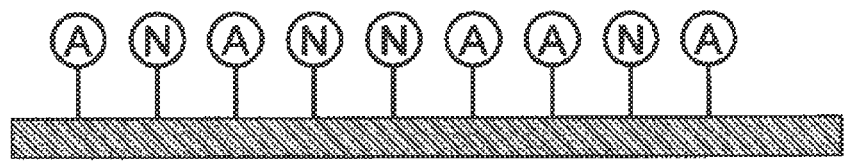
Figure 1:
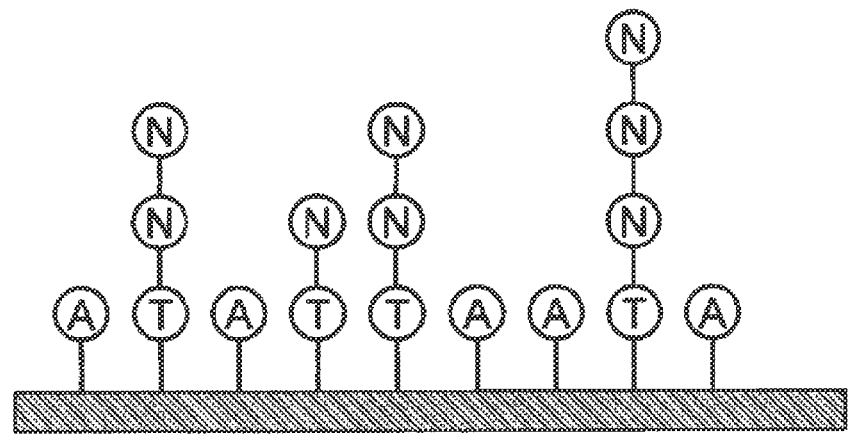
Figure 1:
Figure 1:
Figure 1:
Figure 1:
Figure 2:
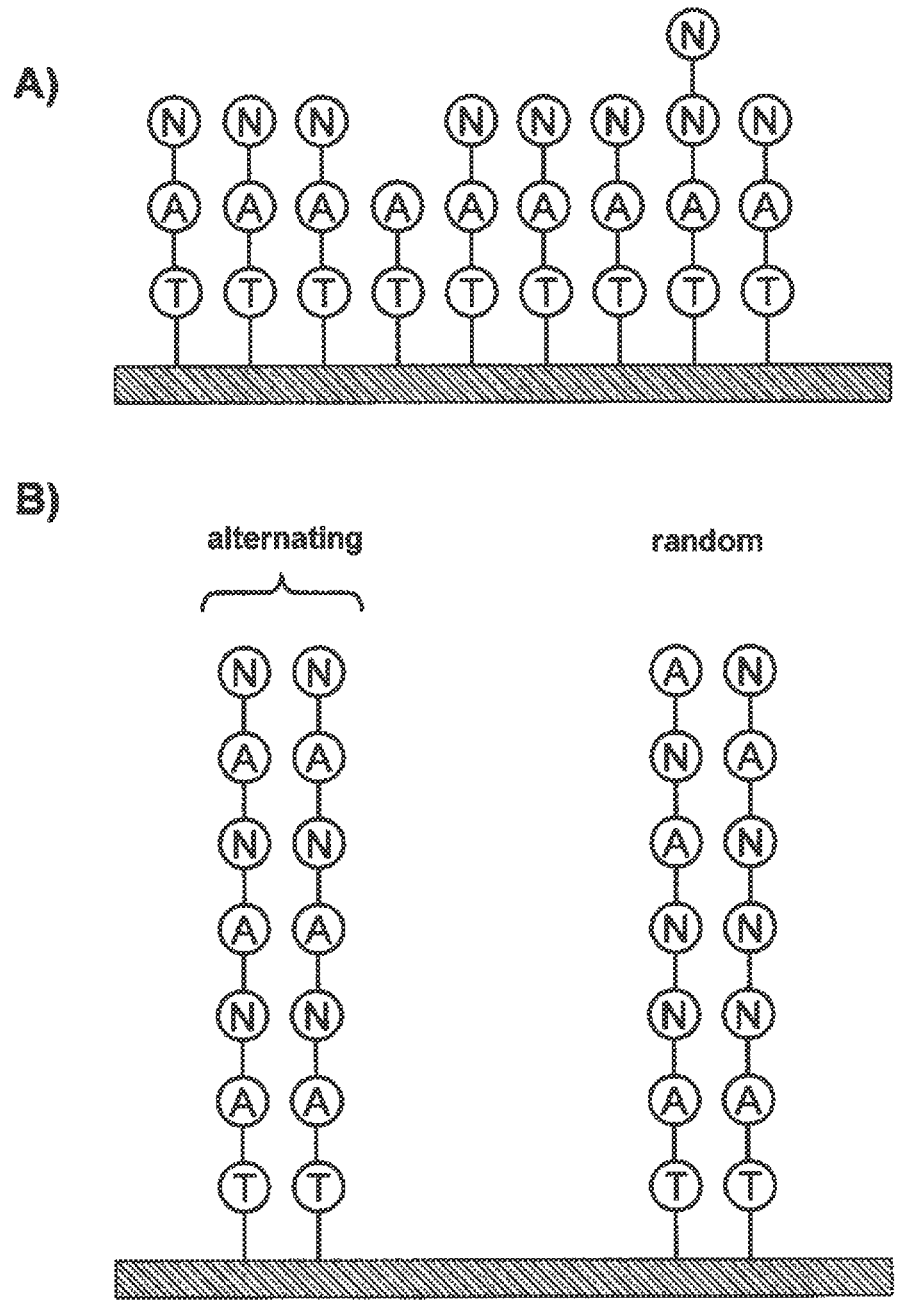
Figure 3:
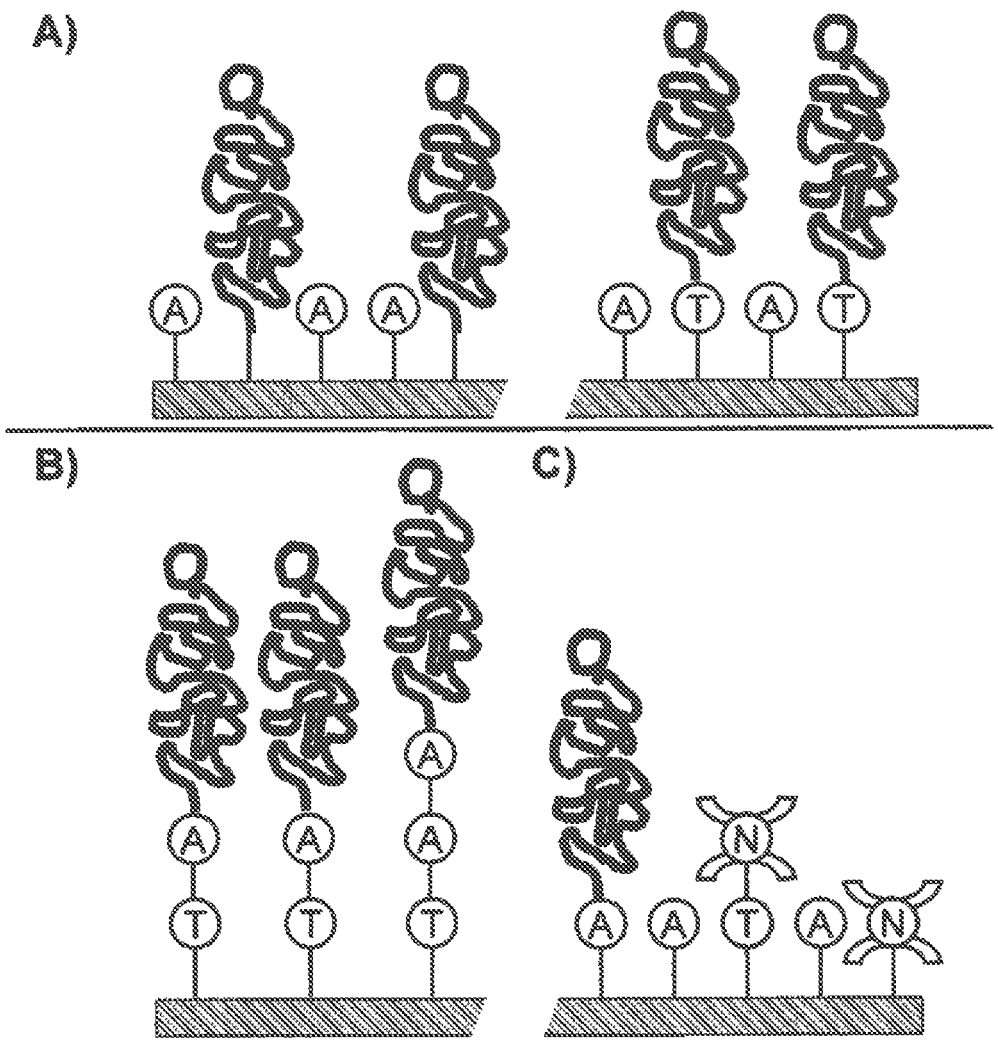
FIG. 3 depicts a schematic overview of the support material being provided with the nucleic acid-binding groups A and the sterically shielding groups N, it being possible for said groups to be combined with the nucleic acid-binding groups A according to the schemes depicted in FIGS. 1 and 2. See Claim 2 (iii).
Figure 3:
Figure 3:
Figure 4:
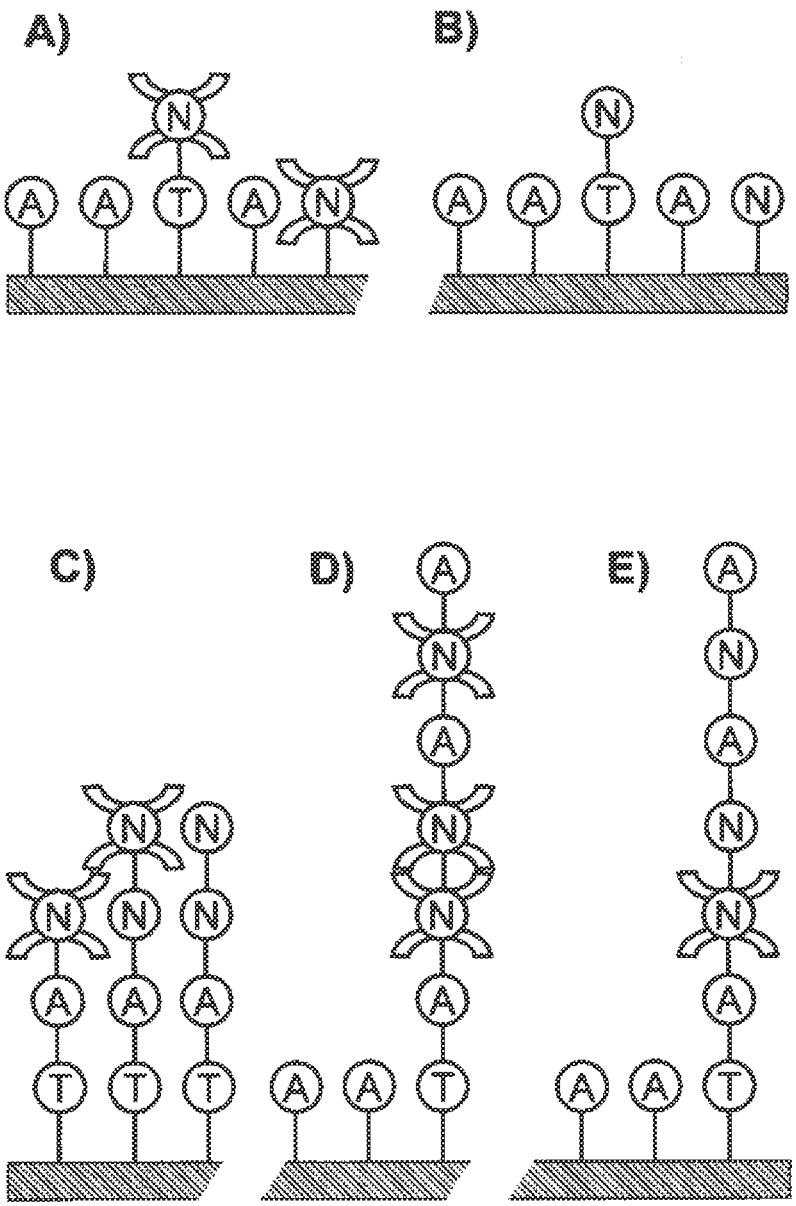
FIG. 4 depicts a schematic overview of the support material being provided by way of example with the nucleic acid-binding groups A and the binding-inhibiting and/or sterically shielding groups N, said groups being formed by a combination of the schemes depicted in FIGS. 1 to 3. See Claim 2 (iv).
Figure 4:
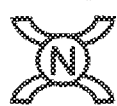
Figure 5:
FIG. 5 depicts a schematic overview of the support material being provided with a substoichiometric amount of nucleic acid-binding groups A. See Claim 3 (iv).
Figure 5:
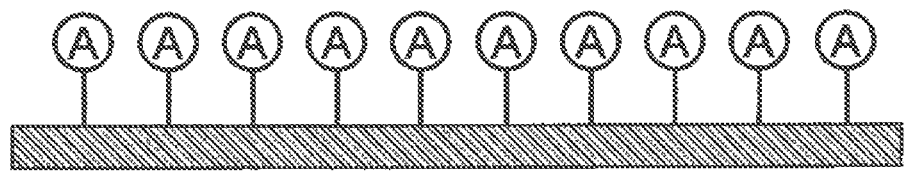
Figure 5:
Figure 5:

The present invention will be illustrated on the basis of some examples below. Said examples are not limiting but are preferred embodiments of the present invention. In addition, all references cited herein are made subject matter of the disclosure.

EXAMPLES

Plasmid DNA was used by way of model systems of nucleic acids in the experiments.

A) Modification of a Support Material with Neighbouring Groups A and N
A.1) Silanization of Silica Gel with 2-(chloromethyl)allyl Trimethoxysilane and DEAPS in a 1:1 Molar Ratio (AAK01-10)
Materials
Support material: Silica/silica gel with a pore size of approx. 150 nm. The specific surface is approx. 25 m²/g.
Coating reagents: 2-(chloromethyl)allyl trimethoxysilane, DEAPS; QSP1 buffers (acidic acetate buffers).

Preparation Protocol
A three-neck flask was charged with 70 ml of water, 2.5 ml of QSP1 buffer (QIAGEN), 322 µl of 2-(chloromethyl)allyl-trimethoxysilane and 413 µl of DEAPS, with a resulting pH of 5.3, and 18 g of silica gel were then added. The mixture was heated with stirring to 95° C. within 20 min, stirred at this temperature for another 4 hours and then cooled with stirring for 1 h. The silica gel was removed via a P3 glass frit and washed successively with 32.3 g of Tris/NaCl buffer, twice with 30 ml of deionized water, twice with 35 ml of methanol and finally with 30 ml of methanol. The final support material, AAK01-10, was dried at 125° C. overnight.

For comparison, the identical support material was modified only with the compound DEAPS bearing the group A. A three-neck flask was charged with 70 ml of water, 2.5 ml of QSP1 buffer, 825 µl of DEAPS, with a resulting pH of 5.5, and 18 g of silica gel were then added. The mixture was heated with stirring to 95° C. within 20 min, stirred at this temperature for another 4 hours and then cooled with stirring for 1 h. The silica gel was removed via a P3 glass frit and washed successively with 32.3 g of Tris/NaCl buffer, twice with 30 ml of deionized water, twice with 35 ml of methanol and finally with 30 ml of methanol. The final support material, AAK01-30, was dried at 125° C. overnight.

Purification of Plasmid DNA Using the Modified Support Material AAK01-10 with Determination of the Point of Elution Binding was carried out in a buffer of 50 mM Tris-HCl, pH 7.0, 15% ethanol. The elution involved running a 0% to 100% step gradient of buffer B (50 mM Tris-HCl, pH 7.0, 15% ethanol, 2M NaCl) over 23 min and determining the amount of eluted DNA continuously by means of UV spectroscopy. The NaCl concentration at which significant amounts of DNA were eluted for the first time was recorded as the point of elution. Introducing the groups N was shown here to significantly lower the point of elution.

The support material coated only with the protonatable groups A (DEAPS) (AAK01-30) exhibits the point of elution at 1600 mM NaCl at pH 7.0. Thus, quite high salt concentrations are required for eluting the nucleic acids. The point of elution of the mixed A/N-modified silica gel, AAK01-10, is at ~700 mM NaCl. The ionic strength required for elution was thus reduced by more than 50%.

A.2) Silanization of the A/N-Modified Silica Gel with Hydroxyethyl Methacrylate (HEMA) (AAK01-11)
Materials
Starting material: modified silica gel AAK01-10 (see protocol A.1)
Coating reagents: Hydroxyethyl methacrylate (HEMA).
Preparation Protocol
HEMA oligomers are synthesized on the previously bound chlorosilane with the aid of the Cu(I)-catalyzed atom transfer radical polymerization (ATRP).

In a reaction flask, 20 ml of HEMA which had been activated via $Al_2O_3$ before and 20 ml of deionized water are rinsed with argon for 30 min, then admixed with 68 mg of $CuCl_2$, 46 mg of $CuBr_2$ and 313 mg of bispyridine, and, after mixing, 10 g of AAK01-20 are added. The mixture is stirred at room temperature for 4 hours and immediately thereafter filtered off with suction via a P3 glass frit. The material on the glass frit is washed first several times with 100 mM NaCl/100 mM EDTA buffer, then with VE water, once with 8 ml of methanol, and twice with 7 ml of methanol. The final support material, AAK01-11, was dried at 60° C. for 14 hours.

For comparison, the DEAPS-modified support material AAK01-30 was reacted with HEMA and worked up in the same way. The final product of this reaction was referred to as AAK01-31. Since DEAPS by way of a functional group bears only a tertiary amine but not a polymerizable allyl group, there should be no HEMA coupling.

Purification of Plasmid DNA Using the Modified Support Material AAK01-11 with Determination of the Point of Elution The experiments were carried out as described under A.1. The support material coated only with the protonatable groups (DEAPS), AAK01-31, exhibits the point of elution at 1500 mM NaCl at pH 7.0. Thus, quite high salt concentrations are required for eluting the nucleic acids. The point of elution of the HEMA-modified silica gel AK01-11 is at ~400 mM NaCl. The ionic strength required for elution was therefore reduced by almost 75%.

A.3) Silanization of Silica Beads with Silanes in Various Molar Ratios.

a) FF Silica Beads

The experimental setup below was chosen. The support material used was FF silica beads.

| | Silane per g of support material | Relative proportions of silanes | | | | pH of elution buffer | DNA eluted by means of elution buffer* per 50 mg of beads [μg] | Remaining bound DNA per 50 mg of beads eluted with QN**-buffer [μg] |
|---|---|---|---|---|---|---|---|---|
| | | SilaneA | | Silane N | | | | |
| | [μmol] | [mmol %] | [μmol] | [mmol %] | [μmol] | | | |
| HL09MB | 182.8 | 25.00 | 45.700 | 75.00 | 137.100 | pH 7.50 | 4.7 | 35.6 |
| HL09MB | 182.8 | 25.00 | 45.700 | 75.00 | 137.100 | pH 7.75 | 20.3 | 29.0 |
| HL09MB | 182.8 | 25.00 | 45.700 | 75.00 | 137.100 | pH 8.00 | 37.3 | 17.3 |
| HL09MB | 182.8 | 25.00 | 45.700 | 75.00 | 137.100 | pH 8.25 | 48.1 | 11.0 |
| HL09MB | 182.8 | 25.00 | 45.700 | 75.00 | 137.100 | pH 8.50 | 52.5 | 7.2 |

*Composition of elution buffer: 20 mM potassium chloride; 50 mM Tris in water, adjusted to pH X;
**Composition of QN buffer: 1600 mM sodium chloride; 50 mM Tris 15% ethanol in water, adjusted to pH 7.

Figure 6:
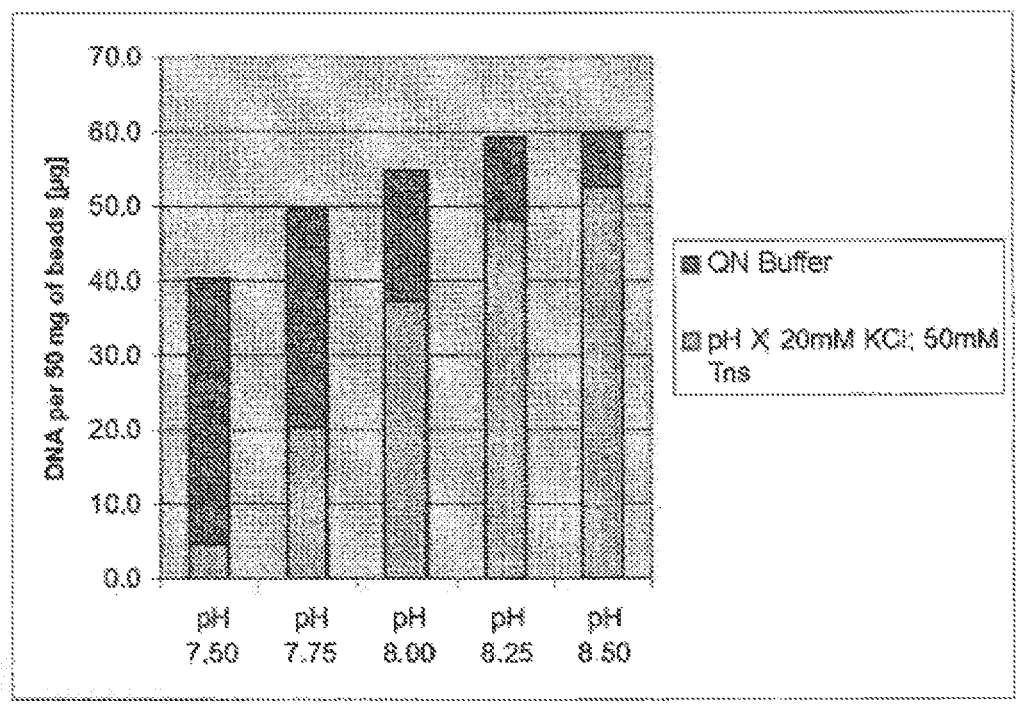
FIG. 6 depicts the elution profile according to Example A 3 a) at different pH values.

The results are depicted in FIG. 6.

b) MAGATTRACT® Beads G (QIAGEN)

The experimental setup below was chosen. The support material used was magnetic silica beads, MAGATTRACT® Beads G from QIAGEN:

| | Silane per g of support material | Relative proportions of silanes | | | | pH-of elution buffer | DNA eluted by means of elution buffer* per 50 mg of beads [μg] | Remaining bound DNA per 50 mg of beads eluted with QN**-buffer [μg] |
|---|---|---|---|---|---|---|---|---|
| | | SilaneA | | Silane N | | | | |
| | [μmol] | [mmol %] | [μmol] | [mmol %] | [μmol] | | | |
| HLG09ST | 182.8 | 25.00 | 45.700 | 75.00 | 137.100 | pH 7.50 | 4.3 | 69.5 |
| HLG09ST | 182.8 | 25.00 | 45.700 | 75.00 | 137.100 | pH 7.75 | 28.6 | 40.9 |
| HLG09ST | 182.8 | 25.00 | 45.700 | 75.00 | 137.100 | pH 8.00 | 50.6 | 15.5 |
| HLG09ST | 182.8 | 25.00 | 45.700 | 75.00 | 137.100 | pH 8.25 | 60.3 | 2.8 |
| HLG09ST | 182.8 | 25.00 | 45.700 | 75.00 | 137.100 | pH 8.50 | 69.0 | 2.7 |

*Composition of elution buffer: 20 mM potassium chloride; 50 mM Tris in water, adjusted to pH X;
**Composition of QN buffer: 1600 mM sodium chloride; 50 mM Tris 15% ethanol in water, adjusted to pH 7.

Figure 7:
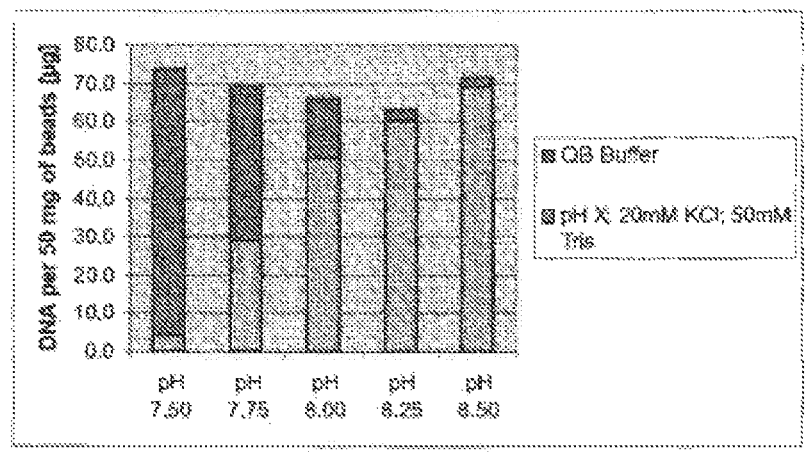
FIG. 7 depicts the elution profile according to Example A 3 b) at different pH values.

The results are depicted in FIG. 7.

B) Modification of a Support Material with Starter Molecules

The random and/or block (co-)polymers according to the invention are prepared by initially applying starter groups T to the appropriate support material—as shown by way of example hereinbelow. Said starter groups are then used in a subsequent step as starting point for applying ligands/polymer chains of groups A and/or groups N.

B.1) Silanization of [3-(2-bromoisobutyryl)propyl]ethoxydimethylsilane on a Silica Gel Materials Support material: silica gel (Fuji MB 1500-40/75/Lot: HT70594)

Coating reagents: [3-(2-bromoisobutyryl)propyl]ethoxydimethylsilane (BPDS)

Amount of silane: 800 μmol/g of support material

Preparation Protocol

A 250 ml KPG stirrer (dry) with reflux condenser and water trap was initially charged with 10.0 g of support material, 200 ml of dry cyclohexane and 2490 mg of [3-(2-bromoisobutyryl)propyl]ethoxydimethylsilane.

The mixture reacted with stirring (100 l/min) at 85° C. (oil bath temperature) overnight (16 h). The oil bath was then removed and the suspension cooled off with stirring within ½ h. The modified support material/silica gel starter (KI04) was removed via a P3 frit and washed thereon with 7×20 ml of hexane. The modified support material was then dried in a vacuum drying cabinet at 40° C. overnight (approx. 12 h).

Five lots of silica gel starters (KI 04 a-e) were prepared according to the above preparation protocol and used as starting point for preparing the weak ion exchangers of the invention in the subsequent step.

C) Preparation of Weak Ion Exchangers by Means of ATRP

The weak ion exchangers of the invention were prepared by allowing random polymer chains of groups A and/or groups N to grow on the starting material, the modified support material carrying starter groups T (KI04).

C.1) Grafting Random Polymers of Groups A/N onto the Modified Support Materials/Silica Gel Starters Described Under B.1

The starting material for this set of experiments was the silica gel starters (KI04d) with BPDS as starter.

To this, the monomers DMAEMA (2-dimethylamino) ethyl methacrylate/group A) and HEMA (hydroxyethyl methacrylate/group N) were applied to one another in the following ratio:

DMAEMA:HEMA
    100:0 → 16.0 mmol:0.0 mmol (KI04d-01)
    50:50 → 8.0 mmol:8.0 mmol (KI04d-03)
    30:70 → 4.8 mmol:11.2 mmol (KI04d-04)
    20:80 → 3.2 mmol:12.8 mmol (KI04d-05)
    10:90 → 1.6 mmol:14.4 mmol (KI04d-07)

Materials
Silica gel starter: KI04d
Monomers: DMAEMA and HEMA
Ligand: 0.96 mmol of 2,2'-bipyridyl (bdy)
Copper salt: 0.48 mmol of copper I bromide (purified)
Solvent: 36 ml of dimethylformamide (DMF)
Starter:Cu(I):ligand ratio=1:4:8
Starter monomer(s) ratio=1:133

Preparation Protocol

A 100 ml three-neck flask with KPG stirrer (glass guide sleeve), argon connection and bubble counter (or connection to diaphragm pump) was initially charged with 150 mg of bdy and 68.8 mg of copper I bromide.

The apparatus was evacuated by means of a diaphragm pump for 1 min and then filled with argon. This procedure was carried out 3 times. Subsequently, a gentle argon stream was permanently passed into the apparatus in order to prevent atmospheric oxygen from entering.

In parallel, 36 ml of DMF (ligand) and the monomers were degassed.

The liquids were then introduced into a two-neck flask with tap, with the monomers having the following initial weight ratios, depending on the preparation:
KI04d-01=2700 µl of DMAEMA:0.0 µl of HEMA
KI04d-03=1350 µl of DMAEMA:972 µl of HEMA
KI04d-04=810 µl of DMAEMA:1360 µl of HEMA
KI04d-05=540 µl of DMAEMA:1555 µl of HEMA
KI04d-07=270 µl of DMAEMA:1750 µl of HEMA The mixture of ligand and monomer(s) was first treated in an ultrasonic bath for 5 min, followed by high vacuum evacuation of the gas space for 5 min.

The ligand-monomer mixture was added by pipetting to the bdy/copper I bromide introduced earlier. The apparatus was evacuated by means of a diaphragm pump for 1 min and then filled with argon. This procedure was carried out 3 times. This was followed by permanently passing a gentle argon stream into the apparatus.

The copper ligand complex was dissolved with stirring (200 l/min) within 15 min. This was followed by adding 1.2 g of the KI 04d silica gel starter.

The apparatus was evacuated by means of a diaphragm pump for 1 min and then filled with argon. This procedure was carried out 3 times. Subsequently, a gentle argon stream was permanently passed into the apparatus.

The mixture was stirred (200 l/min) at 40° C. (oil bath temperature) for 4 h.

The support material with the groups grown thereon (abbreviated to silica gel hereinbelow) was immediately removed via a P3 frit and subsequently washed successively with 5×8 ml of DMF
5×8 ml of THF
5×8 ml of 0.1M EDTA/acetate buffer pH 3.6 (0.2M sodium acetate with glacial acetic acid)
2×8 ml of Tris/NaCl buffer pH 7.0
3×8 ml of water and
3×8 ml of methanol.

The silica gel was then dried to constant weight at 40° C. in a vacuum drying cabinet.

Yield:
KI04d-01=1.31 g
KI04d-03=1.20 g
KI04d-04=1.23 g
KI04d-05=1.29 g
KI04d-07=1.21 g The resulting anion exchangers (the modified support material, or silica gel) and the starting material (the silica gel starter) were studied with regard to their pDNA binding capacity—as will be illustrated in more detail hereinbelow, and corresponding elution profiles were recorded.

The anion exchangers were also tested for CHN content, and from this the polymer chain lengths and the A to N ratio were determined. The (molar) mass ratios of the monomers employed could be shown to be reflected in the resulting silica gel.

Purification of Plasmid DNA Using the Modified Support Material KI04d-01 to KI04d-07, with Determination of the Point of Elution Buffers Used:

|  | pH | [g/l] | [mmol/l] | [g/l] | [mmol] |
|---|---|---|---|---|---|
|  |  | NaCl |  | Sodium acetate trihydrate |  |
| Binding buffer/washing buffer | 5 | 0 | 0 | 6.8 | 50 |
|  |  | KCl |  | Tris |  |
| Elution buffer | 8.5 | 1.49 | 20 | 6.07 | 50 |
|  |  | NaCl |  | Tris |  |
| Tris-NaCl buffer | 10 | 116.88 | 2000 | 6.08 | 50 |

Procedure

Single determinations were carried per silica gel and for either of the two elution buffers.

For this, in each case 50.00 mg (±5 mg) of silica gel were weighed into a 2 ml Safe Lock reaction tube from Eppendorf (referred to as an Eppendorf tube hereinbelow) and, for a DNA solution, 100 µg of pcmvb for each silica gel weighed were admixed with the binding buffer to 1 ml.

Subsequently, 1 ml of DNA solution was added to each of the Eppendorf tubes containing the weighed silica gel, the Eppendorf tubes were sealed and briefly vortexed.

The Eppendorf tubes were then mounted in an end-over-end shaker at medium velocity for 5 min. Shaking was followed by brief centrifugation of the Eppendorf tubes.

The silica gel-DNA suspension was then pipetted, using a truncated tip, into a prepared Tip 20 block with bottom frit (referred to as Tips hereinbelow), below which a 2 ml Eppendorf tube was provided for collecting the supernatant.

In order to capture possible residual material in the Eppendorf tubes, the latter were rinsed out in each case with 0.9 ml of binding buffer which was likewise applied to the corresponding Tips.

Once the liquid had stopped dripping through, all of the remaining liquid was pressed through, and new Eppendorf collecting tubes were placed under the Tip columns.

Subsequently, 1 ml of washing buffer was pipetted into each of the Tips for washing. Once no more liquid dripped through, all of the remaining liquid was pressed through, the Eppendorf collecting tube (containing the wash solution) was put to the side and new Eppendorf collecting tubes were placed under the Tip columns.

Subsequently, 1 ml of the appropriate elution buffer was pipetted into each of the Tips. Here again, once no more liquid dripped through, all of the remaining liquid was pressed through, the Eppendorf collecting tube (containing the eluate) was put to the side and new Eppendorf collecting tubes were placed under the Tip columns.

To detach the remaining bound DNA, 1 ml of Tris-NaCl buffer was pipetted into each of the Tips. Once no more liquid dripped through, all of the remaining liquid was pressed through, the Eppendorf collecting tube (containing the Tris-NaCl solution) was put to the side and the Tip columns were discarded.

To measure the DNA concentration by means of Spectra-Max, in each case 100 µl of the solutions taken were transferred to a UV plate.

The supernatant blank was prepared by mixing 10 µl of EB buffer and 180 µl of binding buffer. 100 µl of this solution were introduced into the UV plate. As a reference to the amount of DNA used, 100 µl of DNA solution were mixed with 90 µl of binding buffer and 100 µl of this solution were introduced into the UV plate.

The blanks used for the eluates were 100 µl of the corresponding elution buffer.

100 µl of Tris-NaCl buffer were used as a Tris-NaCl solution blank.

The NaCl concentration at which significant amounts of DNA were eluted for the first time was recorded as point of elution.

| Silica gels | Monomers in mmol | | | A in % | Points of elution | Total pDNA/ [µg/50 mg] |
|---|---|---|---|---|---|---|
| | A | N | A + N | | | |
| KI 04d-01 | 16 | 0 | 16 | 100 | 1044 | 85 |
| KI 04d-03 | 8 | 8 | 16 | 50 | 928 | 23 |
| KI 04d-04 | 4.8 | 11.2 | 16 | 30 | 738 | 20 |
| KI 04d-05 | 3.2 | 12.8 | 16 | 20 | 582 | 31 |
| KI 04d-07 | 1.6 | 14.4 | 16 | 10 | 370 | 10 |

Figure 8:
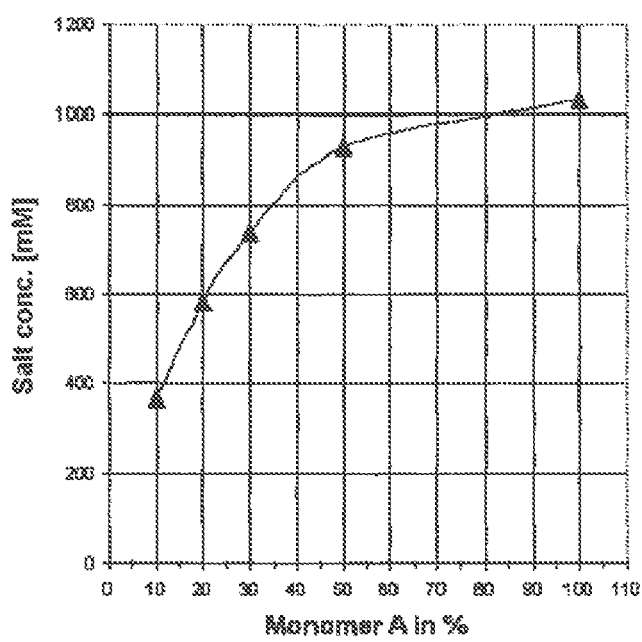
FIG. 8 depicts an elution diagram for the silica gels prepared according to Example C. 1).

Here too, the results (listed in the table above and depicted in FIG. 8) indicated that introducing the groups N significantly lowers the point of elution.

At pH 8.5, the point of elution with the support material/silica gel (KI04d-01) coated only with groups A (DMAEMA) was at 1032 mM NaCl. Thus, fairly high salt concentrations were needed in order to elute the nucleic acids. The point of elution for the mixed A/N-modified silica gel KI04d-05 was at ~580 mM NaCl. The ionic strength required for elution was thus reduced by nearly 50%.

C.2) Grafting Block Polymers of Groups A/N onto the Modified Support Materials/Silica Gel Starters Described Under B.1

The starting material for this set of experiments were the silica gel starters (KI04e) with BPDS as starter.

This was followed by a first step of grafting an amino polymer chain of at least one monomer of group A. And this was followed by a second step of applying to the silica gel prepared in this way a polymer chain of at least one monomer of group N (preferably HEMA).

C.2.1) Step 1

Materials

Silica gel starter: KI04e
Monomers: DMAEMA
Ligand: 7.2 mmol of 2,2'-bipyridyl (bdy)
Copper salt: 3.6 mmol of copper I bromide (purified)
Solvent: 270 ml of dimethylformamide (DMF)
Starter:Cu(I):ligand ratio=1:4:8
Starter:monomer ratio=1:133

Preparation Protocol

A 500 ml three-neck flask with KPG stirrer (glass guide sleeve), argon connection and bubble counter (or connection to diaphragm pump) was initially charged with 1125 mg of bdy and 516 mg of copper I bromide.

The apparatus was evacuated by means of a diaphragm pump for 1 min and then filled with argon. This procedure was carried out 3 times. Subsequently, a gentle argon stream was permanently passed into the apparatus.

In parallel, 270 ml of DMF and 20.25 ml of DMAEMA were degassed. To this end, the two liquids were introduced in a two-neck flask with tap. The mixture was first treated in an ultrasonic bath for 5 min, and this was followed by high vacuum evacuation of the gas space for 5 min.

The DMF-DMAEMA mixture was added to bdy/copper I bromide by pipetting.

The apparatus was evacuated by means of a diaphragm pump for 1 min and then filled with argon. This procedure was carried out 3 times. This was followed by permanently passing a gentle argon stream into the apparatus.

The copper ligand complex was dissolved with stirring (200 l/min) within 15 min. This was followed by adding 9 g of the KI04e silica gel starter.

The apparatus was evacuated by means of a diaphragm pump for 1 min and then filled with argon. This procedure was carried out 3 times. Subsequently, a gentle argon stream was permanently passed into the apparatus.

The mixture was stirred (200 l/min) at 40° C. (oil bath temperature) for 4 h.

The KI04e-01 silica gel with the groups A grown thereon was immediately removed via a P3 frit and subsequently washed successively with
5×60 ml of DMF
5×60 ml of THF
5×60 ml of 0.1M EDTA/acetate buffer pH 3.6 (0.2M sodium acetate with glacial acetic acid)
2×60 ml of Tris/NaCl buffer pH 7.0 and
3×60 ml of water.

The KI04e-01 silica gel was then dried to constant weight at 40° C. in a vacuum drying cabinet.

C.2.2) Step 2

Materials

Silica gel starter: KI04e-01
Monomers: HEMA
Ligand: 0.96 mmol of 2,2'-bipyridyl (bdy)
Copper salt: 0.48 mmol of copper I bromide (purified)
Solvent: 36 ml of dimethylformamide (DMF)
Starter:Cu(I):ligand ratio=1:4:8
Starter monomer ratio=1:200

Preparation Protocol

A 100 ml three-neck flask with KPG stirrer (glass guide sleeve), argon connection and bubble counter (or connection to diaphragm pump) was initially charged with 150 mg of bdy and 68.8 mg of copper I bromide.

The apparatus was evacuated by means of a diaphragm pump for 1 min and then filled with argon. This procedure was carried out 3 times. Subsequently, a gentle argon stream was permanently passed into the apparatus in order to prevent atmospheric oxygen from entering.

In parallel, 36 ml of DMF and 2916 µl of HEMA were degassed. To this end, the two liquids were introduced in a two-neck flask with tap. The mixture was first treated in an ultrasonic bath for 5 min, and this was followed by high vacuum evacuation of the gas space for 5 min.

The DMF-HEMA mixture was added to bdy/copper I bromide by pipetting.

The apparatus was evacuated by means of a diaphragm pump for 1 min and then filled with argon. This procedure was carried out 3 times. This was followed by permanently passing a gentle argon stream into the apparatus.

The copper ligand complex was dissolved with stirring (200l/min) within 15 min. This was followed by adding 1.2 g of the KI04e-01 silica gel starter.

The apparatus was evacuated by means of a diaphragm pump for 1 min and then filled with argon. This procedure was carried out 3 times. Subsequently, a gentle argon stream was permanently passed into the apparatus.

The mixture was stirred (200l/min) at 40° C. (oil bath temperature) for 6 h.

The KI04e-01-01 silica gel with the groups A grown thereon was immediately removed via a P3 fit and subsequently washed successively with
5×8 ml of DMF
5×8 ml of THF
5×8 ml of 0.1 M EDTA/acetate buffer pH 3.6 (0.2M sodium acetate with glacial acetic acid)
2×8 ml of Tris/NaCl buffer pH 7.0
3×8 ml of water and
3×8 ml of methanol.

The KI04e-01-01 silica gel was then dried to constant weight at 40° C. in a vacuum drying cabinet.

The elution experiments carried out with this silica gel could demonstrate that the grafted polymer chain of group N monomers also made a significant contribution to the steric shielding of the nucleic acid(s), thereby significantly reducing the binding strength of said nucleic acid(s).

The invention claimed is:

1. A method of purifying nucleic acids comprising:
(a) binding the nucleic acids to a nucleic acid-binding phase at a binding pH, the nucleic acid binding phase comprising nucleic acid binding groups having a pKa of from 8 to 13 and charge neutral groups having a neutral charge at the binding pH, wherein the binding pH is below the pKa of the nucleic acid-binding groups; and
(b) eluting the nucleic acids at an elution pH which is above the binding pH,
(i) wherein the nucleic acid biding groups are compounds selected from the group consisting of:

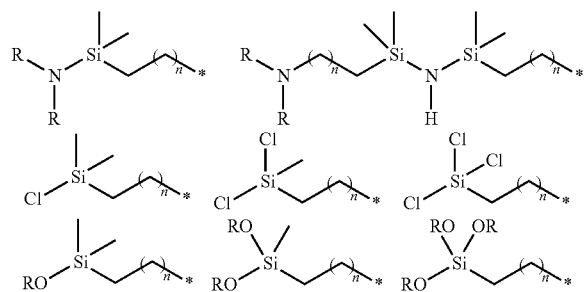

wherein
n is 1 to 5
R is a $C_1$ to $C_6$ alkyl group; and
* is amino, aminomethyl, aminoethyl, aminopropyl, dimethylamino, diethylamino, diisopropylamino, dipropylamino, diethanolamino, dipropanolamino, diethylenetriamine, triethylenetetramine, tetraethylenepentamine, etheramine, polyetheramine, 4-diisobutylamino-1-butane, or 6-dipropylamino-1-hexane, and
(ii) wherein the charge neutral groups are compounds selected from the group consisting of wherein
n is 1-5
R is a C1 to C6 alkyl group;
* is hydroxymethyl, hydroxyethyl, hydroxypropyl, ethanediol, propanediol, propanetriol, butanetriol, 3-glycidoxypropyl, ethyl glycidyl ether, or a $C_1$ to $C_4$ alkyl radical, or halogen.

2. The method according to claim 1, wherein the nucleic acid-binding phase is attached to a support material, wherein only part of the support material comprises the nucleic acid binding groups.

3. The method according to claim 2, wherein
the support material has a silica surface, the amount of nucleic acid binding groups being from 0.1 to 50 µmol.

4. The method according to claim 2, wherein the nucleic acid-binding phase has a support material which complies with one or more of the following features:
(i) the support material is an oxidic material;
(ii) the support material is selected from the group consisting of $Al_2O_3$, $TiO_2$, $ZrO_2$, $Ta_2O_5$, $SiO_2$ and polysilicic acid;
(iii) the support material is $SiO_2$ or polysilicic acid;
(iv) the support material is an organic polymer selected from the group consisting of polystyrene and its derivatives, polyacrylate, polymethacrylate and its derivatives, polyurethane, nylon, polyethylene, polypropylene, polybutylidene and copolymers of these materials;
(v) the support material is a hydrogel;
(vi) the support material is glass or metal; and
(vii) the support material is magnetic.

5. The method according to claim 1, wherein the binding in step (a) and/or the eluting in step (b) are carried out under conditions which comply with one or more of the following features:
(i) in the eluting in (b), the elution pH is below the pKa of the nucleic acid-binding groups;
(ii) the salt concentration in the binding and/or elution buffers is from 1 mM to 1000 mM;
(iii) the salt concentration is unchanged in the binding step (a) and/or in the eluting step (b) or is raised during the eluting;

(iv) the pH in the binding buffer is from pH 2 to pH 8,
(v) the pH in the elution buffer is from pH 2 to pH 10;
(vi) the temperature is unchanged in the binding step (a) and/or in the eluting step (b) or is raised during the eluting; and
(vii) the temperature in the eluting step is from 2° C. to 95° C.

6. The method according to claim 2, wherein one or more of the following features is complied with:
  (i) the support material was prepared with the nucleic acid binding groups and the charge neutral groups by silanization;
  (ii) the nucleic acid binding groups and the charge neutral groups were introduced via reactive silanes;
  (iii) the nucleic acid binding groups and the charge neutral groups were introduced by monofunctional, bi- or tri-functional reactive silanes or a mixture of at least two reactive silanes with different functionality;
  (iv) the nucleic acid binding groups and the charge neutral groups were introduced by reactive silanes selected from the group consisting of aminosilanes, disilazanes, chlorosilanes and alkoxysilanes; and
  (v) the proportion of nucleic acid binding groups based on the charge neutral groups, is from 1% to 99%.

7. The method according to claim 2, wherein one or more of the following features is complied with:
  (i) the support material was modified with starter molecules, with the nucleic acid binding groups and/or the charge neutral groups subsequently being introduced in the form of monomers;
  (ii) the support material was modified with starter molecules, with said starter molecules having one or more of the following features:
    (aa) the starter molecules are reactive silanes; and
    (bb) the starter molecules are selected from the group consisting of

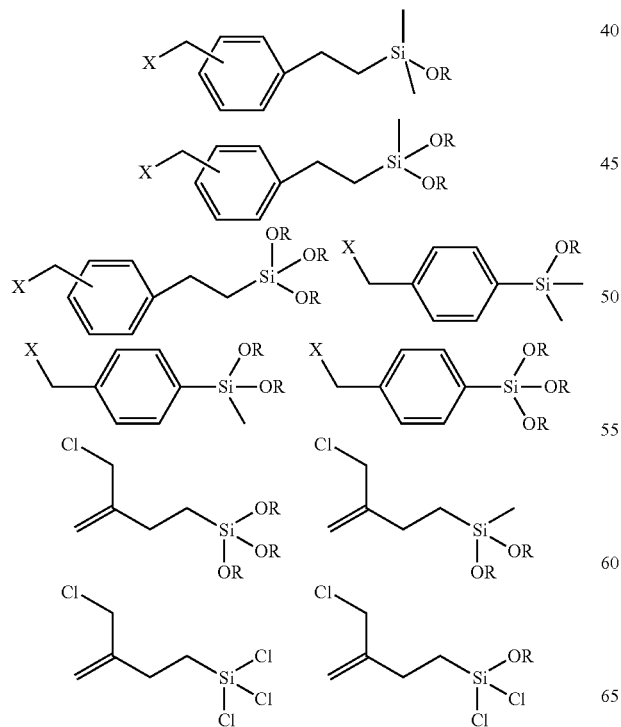

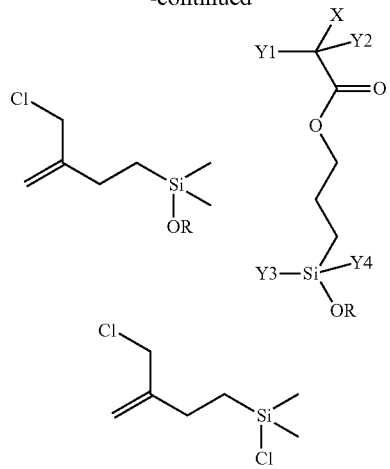

wherein X is halogen
Y1, Y2, Y3 or Y4 are, independently of one another, R, OR, OH or H and R is C1-C3 alkyl;
  (iii) the starter molecule is 2-(chloromethyl)allyl trimethoxysilane;
  (iv) the starter molecule is [3-(2-bromoisobutyryl)propyl] ethoxydimethylsilane;
  (v) the nucleic acid binding groups were introduced by monomers selected from the group consisting of
    N-(3-aminomethyl)methacrylamide, N-(3-aminoethyl)methacrylamide, N-(3-aminopropyl)methacrylamide, N-(3-aminoisopropyl)methacrylamide, N,N-dimethylacrylamide, N,N-diethylacrylamide, N,N-diisopropylacrylamide, N,N-(dimethylamino)ethylacrylamide, N,N-(dimethylamino)ethyl acrylate, N,N-(dimethylamino)ethylmethacrylamide, N,N-(dimethylamino)ethyl methacrylate, N,N-(dimethylamino)propylacrylamide, N,N-(dimethylamino)-propyl acrylate, N,N-(dimethylamino)propylmethacrylamide, N,N-(dimethyl-amino)propyl methacrylate, N,N-(diethylamino)ethylacrylamide, N,N-(diethylamino)ethyl acrylate, N,N-(diethylamino)ethylmethacrylamide, N,N-(diethylamino)ethyl methacrylate, N,N-(diethylamino)propylacrylamide, N,N-(diethylamino)propyl acrylate, N,N-(diethylamino)propylmethacrylamide, N,N-(diethylamino)propyl methacrylate, N,N-(diisopropylamino)ethylacrylamide, N,N-(diisopropylamino)ethyl acrylate, N,N-(diisopropylamino)ethylmethacrylamide, N,N-(diisopropylamino)ethyl methacrylate, N,N-(diisopropylamino)-propylacrylamide, N,N-(diisopropylamino)propyl acrylate, N,N-(dimethylamino)propylmethacrylamide, N,N-(dimethylamino)propyl methacrylate, and 2-(diisopropylamino)ethyl methacrylate;
and
  (vi) the charge neutral groups were introduced by monomers selected from the group consisting of butyl acrylate, propyl acrylate, ethyl acrylate, methyl acrylate, glycidyl methacrylate, hydroxyethyl methacrylate (HEMA), glycidoxypropyl methacrylate, glycerol mono-methacrylate (isomeric mixture), glycol mono-methacrylate, glycidyl acrylate, hydroxyethyl acrylate, glycidoxypropyl acrylate, glycerol mono-acrylate (isomeric mixture), glycol mono-acrylate and N-acryloxysuccinimide.

8. The method according to claim 2, wherein the support material has starter groups which are at least partially functionalized with the nucleic acid binding groups being sterically shielded by the charge neutral groups.

9. The method according to claim 2, wherein the amount of nucleic acid binding groups being from 0.1 to 10 µmol.

10. The method according to claim 5, wherein the salt concentration in the binding and/or elution buffers is from 1 mM to 500 mM.

11. The method according to claim 5, wherein the pH in the binding buffer is from pH 2 to pH 7.5.

12. The method according to claim 5, wherein the pH in the elution buffer is from pH 4 to pH 10.

13. The method according to claim 5, wherein the temperature in the eluting step is from 21° C. to 60° C.

14. The method according to claim 5, wherein the salt concentration in the binding and/or elution buffers is from 1 mM to 250 mM.

15. The method according to claim 5, wherein the pH in the binding buffer is from pH 4 to pH 8.

16. The method according to claim 5, wherein the pH in the elution buffer is from pH 7 to pH 10.

17. The method according to claim 5, wherein the salt concentration in the binding and/or elution buffers is from 1 mM to 100 mM.

18. The method according to claim 5, wherein the pH in the binding buffer is from pH 4 to pH 7.5.

19. The method according to claim 5, wherein the pH in the elution buffer is from pH 8 to pH 9.

20. The method according to claim 6, wherein the proportion of nucleic acid binding groups based on the charge neutral groups, is from 1 to 50%.

21. The method according to claim 6, wherein the proportion of nucleic acid binding groups based on the charge neutral groups, is from 1% to 25%.

* * * * *